United States Patent [19]

Nannini et al.

[11] 4,331,666

[45] May 25, 1982

[54] 3-[(8-CARBOXY-6-TETRAZOLO[1,5-b]PYRIDAZINYL)-THIOMETHYL]-7-[2-(2-AMINO-4-THIAZOLYL)-2-METHOX-YIMINO-ACETAMIDO]-3-CEPHEM-4-CARBOXYLIC ACID

[75] Inventors: Giuliano Nannini; Ettore Perrone, both of Bresso; Ferruccio Casabuona, Monza; Silvio Grasso, Bresso, all of Italy

[73] Assignee: Farmitalia Carlo Erba S.p.A., Milan, Italy

[21] Appl. No.: 138,338

[22] Filed: Apr. 8, 1980

[30] Foreign Application Priority Data

May 11, 1979 [GB] United Kingdom ................ 7916376

[51] Int. Cl.³ .................. A61K 31/545; C07D 501/56
[52] U.S. Cl. ..................................... 424/246; 544/27; 544/236
[58] Field of Search ................... 544/27, 236; 424/246

[56] References Cited

U.S. PATENT DOCUMENTS 4,268,509  5/1981  Teraji et al. ........................ 424/246
4,278,793  7/1981  Durckheimer et al. ............. 544/27

FOREIGN PATENT DOCUMENTS 865632 10/1978 Belgium .
866038 10/1978 Belgium .

*Primary Examiner*—Paul M. Coughlan, Jr.
*Attorney, Agent, or Firm*—Murray and Whisenhunt

[57] ABSTRACT

Heterocyclyl derivatives of oxy-imino-substituted cephalosporins are disclosed, such, for instance the compound 3-[(8-amino-6-tetrazolo[1,5-b]pyridazinyl)-thiomethyl]-7-[2-(2-amino-4-thiazolyl)-2-methox-yimino-acetamido]-3-cephem-4-carboxylic acid and its pharmaceutically and veterinarily acceptable salts. The compounds of the application have high antibacterial activity against Gram-positive and Gram-negative bacteria, including strong beta-lactamase producer Gram-negative microorganisms.

5 Claims, No Drawings

4,331,666

3-[(8-CARBOXY-6-TETRAZOLO[1,5-b]PYRIDAZINYL)-THIOMETHYL]-7-[2-(2-AMINO-4-THIAZOLYL)-2-METHOXYIMINO-ACETAMIDO]-3-CEPHEM-4-CARBOXYLIC ACID

The present invention relates to heterocyclyl derivatives of oxyimino-substituted cephalosporins, to a process for their preparation and to pharmaceutical and veterinary compositions containing them.

The compounds of the invention have the following general formula (I)

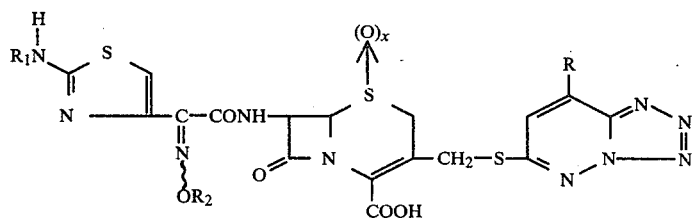

wherein

R represents a group —$(CH_2)_n$—COOR', in which n is zero, 1 or 2 and R' represents a hydrogen atom or a $C_1$–$C_6$ alkyl group; or R represents a

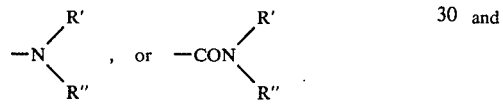

group in which each of the groups R' and R'', which may be the same or different, represents a hydrogen atom or a $C_1$–$C_6$ alkyl group;

$R_1$ represents a hydrogen atom or an amino-protecting group;

$R_2$ represents a hydrogen atom, a hydroxy-protecting group or a branched or straight chain saturated or unsaturated $C_1$–$C_6$ aliphatic hydrocarbon group, which may be unsubstituted or substituted by a substituent selected from (a) hydroxy; (b) cyano; (c) —COOR', in which R' is as defined above and

in which R' and R'' are as defined above; and x is 0, 1 or 2.

The present invention also includes within its scope the pharmaceutically and veterinarily acceptable salts of the compounds of formula (I) as well as all the possible isomers, e.g. syn- and anti-isomers, cis- and trans-isomers and optical isomers, and their mixtures, the metabolites provided with antibacterial activity and the metabolic precursors of the compounds of formula (I).

In the formulae of the invention the wavy line ( { ) means that the oxyimino group may be both in the syn- and in the anti-configuration.

As already said, both the single syn- and anti-isomers of the compounds of formula (I) and their mixtures are included in the scope of the invention.

The chain linked to the carbon atom in the 7-position is always a 7β-chain.

In the compound of formula (I), the 7β-chain may take either or both of the two tautomeric forms

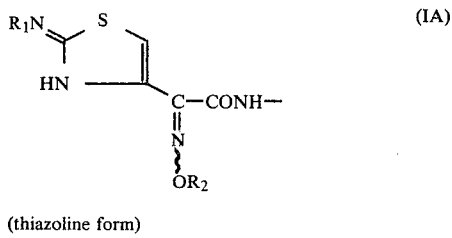

(thiazoline form)

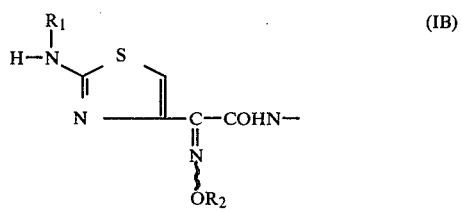

(thiazole form)

This invention includes both the compounds of formula (I) wherein the 7β-chain is in the thiazoline form (IA) and those wherein the 7β-chain is in the thiazole form (IB) as well as the mixtures thereof.

When x is 1 the resulting compounds are sulphoxides and may be in the R or S configuration. When x is 2 the compounds are sulphones.

When $R_1$ is an amino-protecting group it is, for example, one of the protecting groups usually employed in the chemistry of peptides, e.g. formyl, an optionally halogeno-substituted $C_1$–$C_6$ aliphatic acyl, preferably a chloroacetyl or dichloroacetyl, tert-butoxycarbonyl, p-nitrobenzyloxycarbonyl or trityl group.

When $R_2$ is a hydroxy-protecting group it may be, for example, a formyl, acetyl, chloroacetyl, dichloroacetyl, trifluoroacetyl, tetrahydropyranyl, trityl or silyl group, especially trimethylsilyl or dimethyl-tert-butylsilyl.

When $R_2$ is a $C_1$–$C_6$ aliphatic hydrocarbon group, it is preferably $C_1$–$C_6$ alkyl, especially $C_1$–$C_3$ alkyl, or $C_2$ or $C_3$ alkenyl.

A preferred class of compounds of the invention are the syn-isomers of the compounds of formula (I) wherein:

R is —$NH_2$, —$NHCH_3$, —COOH, —$CONH_2$ or —$CH_2COOH$;

$R_1$ is hydrogen;

$R_2$ is hydrogen, methyl, ethyl, —$CH_2$—COOH or

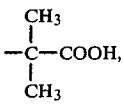

—CH$_2$CN, —CH$_2$—CONH$_2$ or —CH=CH—COOH;

x is zero, 1 or 2;

and pharmaceutically or veterinarily acceptable salts thereof.

A particularly preferred class of compounds of the invention are the syn-isomers of the compounds of formula (I) wherein:

R is —NH$_2$, —COOH or —CH$_2$COOH;
R$_1$ is hydrogen;
R$_2$ is hydrogen, methyl or ethyl;
x is zero;

and pharmaceutically or veterinarily acceptable salts thereof.

More particularly preferred compounds of the invention are the syn-isomers of the compounds of formula (I) wherein:

R is —NH$_2$ or —COOH;
R$_1$ is hydrogen;
R$_2$ is methyl or ethyl;
x is zero;

and pharmaceutically or veterinarily acceptable salts thereof.

Pharmaceutically and veterinarily acceptable salts of the compounds of formula (I) comprise those with inorganic acids, e.g. hydrochloric and sulphuric acid, with organic acids, e.g. citric, tartaric, malic, maleic, mandelic, fumaric and methanesulphonic acid, with inorganic bases, e.g. alkali metal, especially sodium and potassium, alkaline earth metal, especially calcium and aluminium and alkali metal or alkaline earth metal carbonates, salts (these alkaline and alkaline earth metal salts being formable by reaction with hydroxides, carbonates or bicarbonates and the aluminium salt by reaction with aluminium hydroxide) or with organic bases, e.g. organic amines, especially lysine, triethylamine, procaine, dibenzylamine, N-benzyl-β-phenethylamine, (N,N'-dibenzyl)ethylenediamine, dehydroabietylamine, N-ethylpiperidine, diethanolamine, N-methylglucamine, tris(hydroxymethylamino)methane and the like. Also internal salts (i.e. zwitterions) are included in the scope of the invention.

Specific examples of compounds of the invention are the following:

(1) 3-[(8-amino-6-tetrazolo[1,5-b]pyridazinyl)thiomethyl]-7-[2-(2-amino-4-thiazolyl)-2-hydroxyiminoacetamido]-3-cephem-4-carboxylic acid (syn-isomer);

(2) 3-[(8-amino-6-tetrazolo[1,5-b]pyridazinyl)thiomethyl]-7-[2-(2-amino-4-thiazolyl)-2-methoxyiminoacetamido]-3-cephem-4-carboxylic acid (syn-isomer);

(3) 3-[(8-amino-6-tetrazolo[1,5-b]pyridazinyl)thiomethyl]-7-[2-(2-amino-4-thiazolyl)-2-cyanomethoxyiminoacetamido]-3-cephem-4-carboxylic acid (syn-isomer);

(4) 3-[(8-amino-6-tetrazolo[1,5-b]pyridazinyl)thiomethyl]-7-[2-(2-amino-4-thiazolyl)-2-aminocarbonylmethoxyiminoacetamido]-3-cephem-4-carboxylic acid (syn-isomer);

(5) 3-[(8-amino-6-tetrazolo[1,5-b]pyridazinyl)thiomethyl]-7-[2-(2-amino-4-thiazolyl)-2-carboxymethoxyiminoacetamido]-3-cephem-4-carboxylic acid (syn-isomer);

(6) 3-[(8-amino-6-tetrazolo[1,5-b]pyridazinyl)thiomethyl]-7-[2-(2-amino-4-thiazolyl)-2-hydroxyiminoacetamido]-1(R)-sulphinyl-3-cephem-4-carboxylic acid (syn-isomer);

(7) 3-[(8-amino-6-tetrazolo[1,5-b]pyridazinyl)thiomethyl]-7-[2-(2-amino-4-thiazolyl)-2-hydroxyiminoacetamido]-1(S)-sulphinyl-3-cephem-4-carboxylic acid (syn-isomer);

(8) 3-[(8-amino-6-tetrazolo[1,5-b]pyridazinyl)thiomethyl]-7-[2-(2-amino-4-thiazolyl)-2-methoxyiminoacetamido]-1(R)-sulphinyl-3-cephem-4-carboxylic acid (syn-isomer);

(9) 3-[(8-amino-6-tetrazolo[1,5-b]pyridazinyl)thiomethyl]-7-[2-(2-amino-4-thiazolyl)-2-methoxyiminoacetamido]-1(S)-sulphinyl-3-cephem-4-carboxylic acid (syn-isomer);

(10) 3-[(8-amino-6-tetrazolo[1,5-b]pyridazinyl)thiomethyl]-7-[2-(2-amino-4-thiazolyl)-2-hydroxyiminoacetamido]-1-sulphonyl-3-cephem-4-carboxylic acid (syn-isomer);

(11) 3-[(8-amino-6-tetrazolo[1,5-b]pyridazinyl)thiomethyl]-7-[2-(2-amino-4-thiazolyl)-2-methoxyiminoacetamido]-1-sulphonyl-3-cephem-4-carboxylic acid (syn-isomer);

(12) 3-[(8-carboxy-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer);

(13) 3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer);

(14) 3-[(8-aminocarbonyl-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer);

(15) 3-[(8-aminocarbonyl-6-tetrazolo[1,5-b]pyridazinyl)-thiomethyl]-7-[2-(2-amino-4-thiazolyl)-2-methoxy-iminoacetamido]-3-cephem-4-carboxylic acid (syn-isomer);

(16) 3-[(8-methylamino-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer);

(17) 3-[(8-methylamino-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer);

(18) 3-[(8-carboxy-6-tetrazolo[1,5-b]pyridazinyl)-thiomethyl]-7-[2-(2-amino-4-thiazolyl)-2-ethoxyiminoacetamido]-3-cephem-4-carboxylic acid (syn-isomer);

(19) 3-[(8-carboxymethyl-6-tetrazolo[1,5-b]pyridazinyl)-thiomethyl]-7-[2-(2-amino-4-thiazolyl)-2-methoxyimino-acetamido]-3-cephem-4-carboxylic acid (syn-isomer);

(20) 3-[(8-β-carboxyethyl-6-tetrazolo[1,5-b]pyridazinyl)-thiomethyl]-7-[2-(2-amino-4-thiazolyl)-2-methoxyimino-acetamido]-3-cephem-4-carboxylic acid (syn-isomer);

and the pharmaceutically or veterinarily acceptable salts thereof.

The structural formulae of the above-numbered compounds in terms of formula (I) are tabulated below.

TABLE

| Compound | R | $R_1$ | $R_2$ | x |
|---|---|---|---|---|
| 1 | —$NH_2$ | H | H | zero |
| 2 | —$NH_2$ | H | —$CH_3$ | zero |
| 3 | —$NH_2$ | H | —$CH_2CN$ | zero |
| 4 | —$NH_2$ | H | —$CH_2CONH_2$ | zero |
| 5 | —$NH_2$ | H | —$CH_2$—COOH | zero |
| 6 | —$NH_2$ | H | H | 1(R) |
| 7 | —$NH_2$ | H | H | 1(S) |
| 8 | —$NH_2$ | H | —$CH_3$ | 1(R) |
| 9 | —$NH_2$ | H | —$CH_3$ | 1(S) |
| 10 | —$NH_2$ | H | H | 2 |
| 11 | —$NH_2$ | H | —$CH_3$ | 2 |
| 12 | —COOH | H | H | zero |
| 13 | —COOH | H | —$CH_3$ | zero |
| 14 | —$CONH_2$ | H | H | zero |
| 15 | —$CONH_2$ | H | —$CH_3$ | zero |
| 16 | —$NHCH_3$ | H | H | zero |
| 17 | —$NHCH_3$ | H | —$CH_3$ | zero |
| 18 | —COOH | H | —$C_2H_5$ | zero |
| 19 | —$CH_2COOH$ | H | —$CH_3$ | zero |
| 20 | —$(CH_2)_2COOH$ | H | —$CH_3$ | zero |

The compounds of the invention can be prepared by a process comprising:

(A) reacting a compound of formula (II)

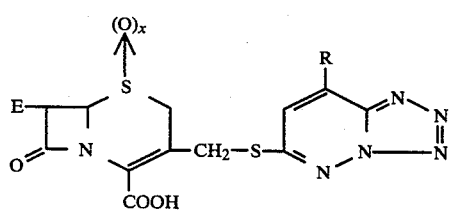

wherein x and R are as defined above and E represents an amino group or a group of formula —N=C=Y wherein Y is oxygen or sulphur, or a reactive derivative thereof, with a compound of formula (III)

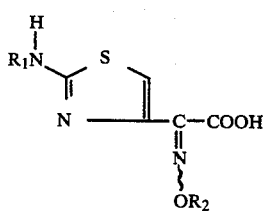

wherein $R_1$ and $R_2$ have any of the meanings defined above except hydrogen, or a reactive derivative of such a compound of formula (III) and, if desired, removing the protecting groups, where present; or (B) reacting a compound of formula (IV)

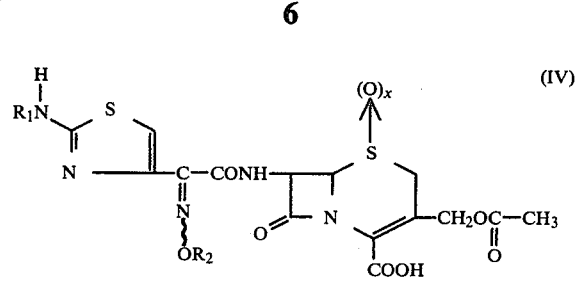

wherein $R_1$, $R_2$ and x are as defined above, or a salt thereof, with a compound of formula (V)

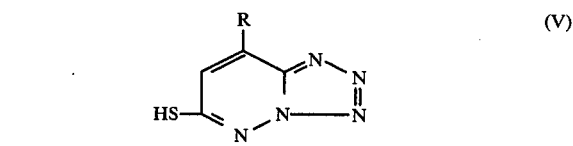

wherein R is as defined above, or a reactive derivative of such a compound of formula (V) and, if desired, removing the protecting groups, where present; or (C) reacting a compound of formula (VI)

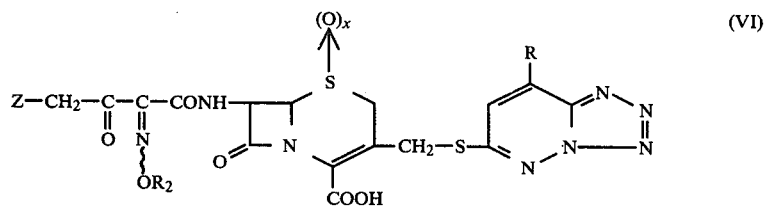

wherein R, $R_2$ and x are as defined above and Z represents a halogen atom, or a salt or ester thereof, with thiourea, thus giving a compound of formula (I) wherein $R_1$ is hydrogen and, if desired, removing the protecting group possibly present in $R_2$; and/or, if desired, converting a compound of formula (I) into a salt thereof or obtaining a free compound from a salt and/or, if desired, resolving a mixture of isomers into the single isomers and/or, if desired, converting a compound of formula (I) into another compound of formula (I).

In the compounds having the formulae (II), (IV), (VI), the free carboxy groups may be protected, if necessary, in a conventional manner before the reaction takes place. Examples of protecting groups are those usually employed in the synthesis of peptides, for example, tert-butyl, benzhydryl, p-methoxybenzyl, p-nitrobenzyl, trityl and trialkylsilyl. The protecting groups can then be removed, at the end of the reaction, in a known manner, e.g. by mild acid hydrolysis or by catalytic hydrogenation, for example with Pd/C at room pressure. Since, however, compounds of formula (I) containing the said protecting groups are included in the present invention, removal of the protecting groups is not an essential process step.

The starting materials used in each of the above-mentioned processes (A) to (C), when one or more asymmetric carbon atoms are present, may be either optically active or racemic compound. Furthermore, the starting materials may be syn- or anti-isomers and their mixtures, as well as cis- or trans-isomers and their mixtures.

A reactive derivative of the compound of formula (II) may be, for example, an amine salt, a silyl ester or a metal salt. A reactive derivative of the compound of formula (III) is, for example, an acyl halide, an anhydride, a mixed anhydride, an azide, a reactive ester or a salt, for instance a salt formed with alkaline metals or alkaline earth metals, ammonia or an organic base. A reactive ester may be, for example, p-nitrophenyl ester, 2,4-dinitrophenyl ester, pentachlorophenyl ester, N-hydroxysuccinimide ester and N-hydroxyphthalimide ester.

In the compound of formula (VI) Z is preferably chlorine or bromine.

A salt of a compound of formula (VI) is, for example, an alkaline or alkaline earth metal salt of the —COOH group in the compound. Also, the free carboxy, carboxymethyl or carboxyethyl groups possibly represented by the R substituent may be analogously salified.

The reaction between the compound of formula (II) or a reactive derivative thereof and the compound of formula (III) or a reactive derivative thereof may be performed either at room temperature or under cooling, preferably from about $-50°$ C. to about $+40°$ C., in a suitable solvent, e.g. acetone, dioxane, tetrahydrofuran, acetonitrile, chloroform, methylene chloride, N,N-dimethylformamide, 1,2-dichloroethane or in a mixture of water and a solvent miscible with water and, if necessary, in the presence of a base, for example sodium bicarbonate, potassium bicarbonate or a trialkylamine, or in the presence of another acid acceptor, such as an alkylene oxide, e.g. propylene oxide.

When the compound of formula (III) is reacted with the compound of formula (II) wherein E is amino, as a free acid or as a salt, it is desirable that the reaction be performed in the presence of a condensing agent, for instance N,N'-dicyclohexylcarbodiimide. The optional removal of the protecting groups, at the end of the reaction, may be performed in a known manner. For example, the tert-butoxycarbonyl group may be removed by treatment with an aqueous solution of an acid (for example HCl or $H_2SO_4$) and the monochloroacetyl group may be removed by treatment with thiourea. The formyl and the trifluoroacetyl groups may be removed by treatment with potassium bicarbonate in aqueous methanol; the tetrahydropyranyl group by treatment with dilute hydrochloric acid; and the trityl group by treatment with formic or trifluoroacetic acid.

The reaction between the compound of formula (IV) and the heterocyclic thiol of formula (V) may be carried out in water or a mixture of water and an organic solvent e.g. acetone, ethanol, dioxane or tetrahydrofuran, in the presence of about 2 equivalents of a base, for example sodium bicarbonate. The reaction temperature preferably ranges from about 5° C. to about 90° C. and the pH is preferably maintained from about 5 to about 7.5. If desired, a buffer may be used, for example sodium phosphate or acetate. In a different way, the same reaction may be performed without any base and in a strictly anhydrous solvent, at temperatures ranging from about 50° C. to about 120° C., and for reaction times ranging from a few hours to a few days. The preferred solvent is acetonitrile, and an inert atmosphere (e.g. nitrogen) may be advisable in order to prevent the oxidation of the heterocyclic thiol (V). The subsequent optional removal of the protecting groups may be performed by known methods, e.g. those indicated above.

The reaction between the compound of formula (VI) or a salt or an ester thereof with thiourea is preferably carried out in an aprotic solvent e.g. N,N-dimethylformamide, N,N-dimethylacetamide, dimethylsulphoxide, acetonitrile, hexamethylphosphorotriamide, or in a mixture of these solvents. The reaction temperature preferably ranges from about 0° C. to about 90° C. The subsequent optional removal of the protecting group possibly present as $R_2$ may be carried out as indicated above.

Both the optional conversion of a compound of formula (I) into a salt thereof and the preparation of a free compound from a salt or ester as well as the optional resolution of a mixture of isomers into the single isomers and the optional conversion of a compound of formula (I) into another compound of formula (I) may be carried out by known methods. Thus, for example, the compounds of formula (I) wherein x is 1 and wherein the sulphoxide is in the S configuration, may be preferably obtained from the corresponding compounds of formula (I) wherein x is zero by treatment with an oxidizing agent especially a peracid, for example perbenzoic acid, permaleic acid, sodium periodate, hydrogen peroxide or a mixture of these, with an inorganic or organic acid e.g. formic acid, acetic acid or trifluoroacetic acid. The reaction may be performed in a solvent, e.g., dioxane, tetrahydrofuran, chloroform, methylene chloride, formic acid, acetic acid, benzene, N,N-dimethylformamide, N,N-dimethylacetamide or the like. The reaction temperature is preferably from about $-30°$ C. to about $+90°$ C.

To obtain the sulphoxide with the R configuration, it is preferable to carry out the same oxidation reaction on the intermediate products, preferably on the compounds of formula (II) wherein E is amino, after first protecting this amino group by formation of a Schiff base. The Schiff base may be prepared by known methods e.g. by treatment of the amine of formula (II) with an aldehyde such as benzaldehyde, salicylaldehyde or p-nitrobenzaldehyde; at the end of the oxidation reaction the free amino group may be obtained for example by treatment with a hydrazine derivative, for instance phenylhydrazine, 2,4-dinitrophenylhydrazine, or a Girard reagent. The carboxyl group is preferably protected during the oxidation reaction using e.g. as protecting groups those mentioned above.

The conversion of sulphide to sulphoxide, i.e. the conversion of a compound of formula (I) wherein x is zero into the corresponding compound wherein x is 1, may be effected by using 1–1.2 molar equivalents of the oxidizing agent for each mole of the compound to be oxidized.

The conversion of sulphide to sulphone, i.e. the conversion of a compound of formula (I) wherein x is zero into the corresponding compound of formula (I) wherein x is 2 may be performed by the same oxidizing agents used to obtain the sulphoxides, using in this case at least two molar equivalents of the oxidizing agent for each mole of the compound to be oxidized.

The compound of formula (II) wherein E is amino and x is zero, may be prepared, for example, by reacting 7-amino-cephalosporanic acid or a salt thereof with a compound of formula (V), using reaction conditions well known in literature.

The compound of formula (II) wherein E is —N=C=Y and x is zero may be prepared by reacting a compound of formula (II) wherein E is amino and x is zero with phosgene or thiophosgene, in the presence of a hydrochloric acid acceptor, using known methods.

The compounds of formula (III) are known compounds or may be prepared by known methods.

The compounds of formula (IV) wherein x is zero may be prepared, for example, by reacting 7-aminocephalosporanic acid or a salt thereof with a compound of formula (III) or a reactive derivative thereof using reaction conditions analogous to those described above for the reaction between the compound of formula (II) and the compound of formula (III).

The compounds of formula (VI) wherein x is zero, may be prepared, for example, by reacting a compound of formula (II) wherein E is amino and x is zero, with a compound of formula (VII)

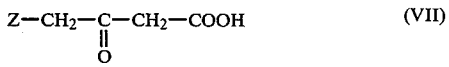

wherein Z is as defined above, or a reactive derivative thereof, e.g. one of the reactive derivatives indicated above for the compound of formula (III), using reaction conditions analogous to those indicated for the reaction between the compound of formula (II) and the compound of formula (III). A compound thereby obtained of formula (VIII)

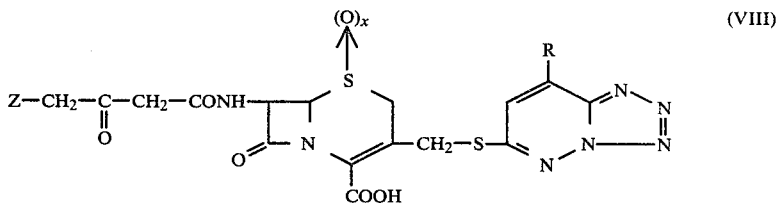

(VIII)

wherein Z and R are as defined above and x is zero, may be transformed into a compound of formula (VI) wherein $R_2$ is hydrogen, by nitrosation, e.g. using as a nitrosating agent, nitrosyl chloride or an organic or inorganic nitrite, for instance amyl nitrite, sodium nitrite or potassium nitrite, in the presence of an acid, for instance hydrochloric acid or acetic acid. The nitrosation reaction may be performed at room temperature or under cooling, the preferred temperature range being from about $-20°$ C. to about $40°$ C., in a suitable solvent, e.g. dioxane, acetonitrile, tetrahydrofuran, acetic acid or a mixture of one of these solvents with water. Before the nitrosation, the carboxyl groups present may be, if necessary, converted into salt form, e.g. by treatment with an alkaline metal hydroxide, or protected e.g. by a protecting group mentioned above; the protecting groups may be then removed by known methods at the end of the reaction.

The compounds of formula (VI) wherein $R_2$ is other than hydrogen may be obtained starting from the corresponding compounds wherein $R_2$ is hydrogen by a usual etherification or esterification reaction.

The compounds having the formulae (II), (IV) and (VI) wherein x is 1 or 2, may be obtained by oxidizing the corresponding compounds wherein x is zero as described above for the analogous conversions on the compounds of formula (I).

When the starting materials of formula (III), (IV) and (VI) are syn-isomers, the reaction products are syn-isomers too and vice-versa. In some cases a little amount of the anti-isomer might be obtained together with the syn-isomer. The separation of the isomers may be performed by known methods, e.g. by fractional crystallisation or by chromatography. The compounds of the present invention have a high antibacterial activity either in animals or humans not only against Gram-positive and Gram-negative bacteria normally susceptible to cephalosporins such as staphylococci, streptococci, diplococci, Klebsiella, *Escherichia coli, Proteus mirabilis,* Salmonella, Shigella, Haemophilus and Neisseria, but also against the strong beta-lactamase producer Gram-negative micro-organisms, such as, for example, *Klebsiella aerogenes* 1082 E, *Escherichia coli* Tem, *Enterobacter cloacae* P 99, indole-positive Proteus and the like, as well as against *Pseudomonas aeruginosa* strains, which are normally resistant to most cephalosporins. These compounds are therefore particularly suitable for the treatment of the infections caused by Gram-negative bacteria, for example, urinary tract infections and respiratory tract infections.

The activity of the compounds of the invention both against bacteria normally susceptible to cephalosporins and against beta-lactamase producers is higher than that of Cefazolin and Cefuroxime.

For example, compound 3-[(8-amino-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer) (designated as FCE 20127) is about 24 times more active than Cefazolin against streptococci and about 30 times more active than Cefazolin and Cefuroxime against most Gram-negative bacteria. Besides, compound FCE 20127 is about from 20 to 60 times more active than Cefuroxime against some beta-lactamase producers, such as *Klebsiella aerogenes* 1082 E, *Enterobacter cloacae* P 99, *Escherichia coli* Tem.

Compound FCE 20127 was also tested on a series of 10 strains of *Pseudomonas aeruginosa,* 4 strains of *Proteus vulgaris* and 4 strains of *Proteus morganii* and it was found to be several times more active than Cefazolin and Cefuroxime.

Compound 3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer) (designated as FCE 20485) is about 5 times more active than Cefazolin against streptococci and about 32 times more active than Cefazolin and 40 times more active than Cefuroxime against most Gram-negative bacteria. Against *Enterobacter aerogenes* ATCC 8308, *Enterobacter cloacae* 1321 E, *Salmonella typhi* Watson and *Shigella sonnei* ATCC 11060 the compound FCE 20485 is from 15 to 50 times more active than Cefazolin and from 50 to 100 times more active than Cefuroxime.

Besides compound FCE 20485 is at least from 100 to 500 more active than Cefazolin and Cefuroxime against *Proteus vulgaris* X 20 and *Proteus mirabilis* ATCC 9921. Compound FCE 20485 showed also a significant in vitro activity against *Pseudomonas aeruginosa* G. and *Bacteroides fragilis* VPL 9032.

Another important property of compound FCE 20485 is the very long plasma half-life in the mouse (about 90 minutes) and in the rat (about 100 minutes) after intravenous injection, while the plasma half-life of Cefazolin is respectively 16 and 20 minutes. Consequently, compound FCE 20485 showed a high activity in vivo tests; for example, in mice infected with *Escherichia coli* G, *Klebsiella pneumoniae* ATCC 10031, *Proteus mirabilis* ATCC 9921, *Escherichia coli* Tem., *Haemophilus influenzae Salmonella typhi* Watson and *Proteus vulgaris* X 20, the compound was from 20 to 200 times more active than Cefazolin.

The toxicity of the compounds of the invention is quite negligible and therefore they can be safely used in therapy. For example, the approximate acute toxicity ($LD_{50}$) of compounds FCE 10127 and FCE 20485 in the mouse determined with single intravenous administrations of increasing doses and measured on the seventh day of treatment is greater than 2000 mg/kg. Analogous activity and toxicity data have been found for the other compounds of the invention.

The compounds of the invention are therefore useful in the treatment of the infections caused by either gram-positive or gram-negative microorganisms, such as respiratory tract infections, for example, bronchitis, bronchopneumonia, pleurisy; hepatobiliary and abdominal infections, for example, cholecystitis, peritonitis; blood and cardiovascular infections, for example, septicemia; urinary tract infections, for example, pyelonephritis, cystitis; obstetrical and gynecological infections, for instance, cervicitis, endometritis; ear, nose and throat infections, for instance, otitis, sinusitis, parotitis. The compounds of the invention may be administered, either to humans or to animals, in a variety of dosage forms, e.g. orally in the form of tablets, capsules, drops or syrups; rectally in the form of suppositories; parenterally, e.g., intravenously or intramuscularly (as solutions or suspensions), intravenous administration being preferred in an emergency situation; by inhalation in the form of aerosols or solutions for nebulizers; intravaginally in the form, e.g. of bougies; or topically in the form of lotions, creams and ointments.

The invention includes a pharmaceutical or veterinary composition containing a compound of the invention in association with a pharmaceutically or veterinarily acceptable excipient. Such compositions may be prepared in a conventional way be employing the conventional excipients, usually carriers and/or diluents, used for the other cephalosporins. Conventional carriers or diluents are, for example, water, gelatine, lactose, starches, magnesium stearate, talc, vegetable oils, cellulose and the like. Daily doses in the range of about 1 to about 100 mg per kg of body weight may be used, in various animal species, the exact dose depending on the age, weight and condition of the subject to be treated and on the frequency and route of administration. A preferred mode of administration of the compounds of the invention is the parenteral one; in this case compounds may be administered to adult humans in an amount from about 100 mg to 200 mg per dose, preferably about 150 mg per dose, 1–4 times a day, dissolved in a suitable solvent, for example, sterile water or lidocaine hydrochloride solution, for intramuscular injections, and sterile water, physiological saline solutions, dextrose solution or the conventional intravenous fluids or electrolytes, for intravenous injections.

Furthermore, the compounds of the invention may be used as antibacterial agents in a prophylactic manner, e.g. in cleaning or as surface disinfecting compositions, for example, at a concentration of about 0.2 to 1% by weight of such compounds admixed with, suspended or dissolved in conventional inert dry or aqueous carriers for application by washing or spraying. They are also useful as nutritional supplements in animal feeds.

The following examples illustrate the invention. Assessment of melting points was somewhat difficult in some cases, as the compounds tend to retain the solvent.

The I.R. spectra were determined in a solid phase (KBr) or Nujol ® on a Perkin-Elmer 125 spectrophotometer, while the U.V. spectra were evaluated in a buffer phosphate solution at pH 7.4 or in 1% $NaHCO_3$ on a Bausch-Lomb apparatus.

N.M.R. spectra were determined with a Bruker HX-90 (90 MHz) for the final compounds and with a Perkin-Elmer R-24B (60 MHz) for the intermediate ones in DMSO (dimethylsulphoxide) or $CDCl_3$ with $(CH_3)_4Si$ as internal standard.

EXAMPLE 1

3-[(8-Amino-6-tetrazolo-[1,5-b]-pyridazinyl)thiomethyl]-7-[2-(2-amino-4-thiazolyl)-2-methoxyiminoacetamido]-3-cephem-4-carboxylic acid (syn-isomer)

A stirred solution of anhydrous methylene chloride (70 ml) containing 2-(2-tritylamino-4-thiazolyl)-2-methoxyiminoacetic acid (syn-isomer) (4.43 g; 0.01 mole) and triethylamine (1.41 ml; 0.01 mole), was cooled to 0° C., and phosphorus pentachloride (2.08 g; 0.01 mole) was added portionwise. After 10 minutes of stirring at 0° C. and 1 hour at room temperature, the mixture was evaporated under reduced pressure, taken up in acetone/benzene, evaporated again in order to remove any traces of phosphorus oxychloride, and taken up in 50 ml of anhydrous acetone. Triethylamine hydrochloride was then removed by filtration. The acetone solution of 2-(2-tritylamino-4-thiazolyl)-2-methoxyiminoacetyl chloride thus obtained was dropped into a vigorously stirred, ice-cooled solution of 7-amino-3-[(8-amino-6-tetrazolo-[1,5-b]pyridazinyl)thiomethyl]-3-cephem-4-carboxylic acid (3.8 g; 0.01 mole), $NaHCO_3$ (0.84 g) and triethylamine (2.82 ml) in a mixture of water and acetone (75 ml:50 ml). The slurry was stirred for ½ hour at 0°–5° C. and then for 1½ hours at room temperature, taken up in ethyl acetate (500 ml), washed with dilute hydrochloric acid (50 ml), then aqueous sodium chloride (100 ml), dried with sodium sulphate and evaporated to dryness. The residue was stirred in methylene chloride (5 ml); then ethyl acetate (50 ml) and diethyl ether (50 ml) were added. The precipitated produced was collected, dissolved in warm methylene chloride (30 ml), cooled and treated with stirring with diethyl ether (100 ml). After 20 minutes of stirring, the white solid was filtered, washed with ether and dried, thus giving 4.3 g of 3-[(8-amino-6-tetrazolo[1,5-b]pyridazinyl)-thiomethyl]-7-[2-(2-tritylamino-4-thiazolyl)-2-methoxyiminoacetamido]-3-cephem-4-carboxylic acid (syn-isomer) as a white powder.

The above-mentioned compound (2.0 g) was added portionwise to a stirred, hot (55° C.) solution of formic acid (13 ml) in water (13 ml). Stirring and heating at the same temperature was maintained for 25 minutes, and then the solid was filtered from the cooled mixture. The solid was triturated in 99% formic acid (10 ml), then water (2 ml) was added and pure triphenylmethanol was filtered off.

The acidic mother liquors were combined and evaporated, leaving a residue. After complete removal of water and formic acid, followed by trituration with anhydrous ethanol, a solid was obtained (1,225 g). The crude product was suspended in water (70 ml) and enough NaHCO$_3$ was added to give a solution. The pH of the solution was lowered to 2.0 by adding 2 N HCl and after 20 minutes the precipitated product was collected, washed thoroughly with water, and dried for 18 hours at 75° C. There was thus obtained 1.13 g of the title compound, which decomposed without melting at above 225° C.

Elemental analysis: Found: C, 37.90; H, 3.14; N, 26.78; S, 16.83. Calculated for C$_{18}$H$_{17}$N$_{11}$O$_5$S$_3$: C, 38.35; H, 3.04; N, 27.33; S, 17.07.

I.R. (KBr): 3320–3180 NH
[cm$^{-1}$]    1760    $\diagdown$C=O ($\beta$-lactam)
                       $\diagup$ 1520    —CONH—  (sec.amide)
1030    =N—O—CH$_3$ NMR, 100 MHz (DMSO-d$_6$):
[$\delta$,p.p.m.]
3.74 (2H,d.d.,2-CH$_2$)    J $\simeq$ 17 H$_z$
3.88 (3H,s.,—OCH$_3$)
4.36 (2H,d.d.,3-CH$_2$S)    J $\simeq$ 13 H$_z$
5.20 (1H,d.,6-H)    J $\simeq$ 5 H$_z$
5.83 (1H,d.d.,7-H)    J $\simeq$ 5 H$_z$ + 8 H$_z$
6.41 (1H,s.,7-H on pyridazine ring)
6.82 (1H,s.,5-H on thiazole ring)
6.80–7.80 (2H,broad s.,—NH$_2$ on thiazole ring)
8.02 (2H, broad s.,—NH$_2$ on pyridazine ring)
9.69    J $\simeq$ 8 H$_z$
(1H,d.,—CONH—)

EXAMPLE 2

3-[(8-aminocarbonyl-6-tetrazolo[1,5-b]pyridazinyl)-thiomethyl]-7-[2-(2-amino-thiazolyl)-2-methoxyiminoacetamido]-3-cephem-4-carboxylic acid (syn-isomer) was obtained by reacting 2-(2-tritylamino-4-thiazolyl)-2-methoxyimino-acetic acid with 7-amino-3-[(8-aminocarbonyl-6-tetrazolo[1,5-b]pyridazinyl)-thiomethyl]-3-cephem-4-carboxylic acid using the method reported in example 1, m.p. 220° C. (dec.)

Elemental Analysis: found: C, 38.71; H, 2.96; N, 25.81; S, 16.01; calculated for C$_{19}$H$_{17}$N$_{11}$O$_6$S$_3$: C, 38.57;H, 2.89; N, 26.04; S, 16.26.

T.L.C. (CHCl$_3$:MeOH:HCOOH:H$_2$O=140:75:20:20) R$_f$=0.42

I.R. (KBr)    $\diagdown$C=O   $\beta$-lactam
              $\diagup$ 7-amino-3-[(8-aminocarbonyl-6-tetrazolo[1,5-b]pyridazinyl)-thiomethyl]-3-cephem-4-carboxylic acid, used as starting material, was prepared as follows:

6-chloro-8-aminocarbonyl-tetrazolo[1,5-b]pyridazine

To an ice-cold solution of 3-hydrazino-4-aminocarbonyl-6-chloro-pyridazine (4.2 g; 0.0244 mole) [obtained as reported in J. Het. Chemistry, 7, 465 (1970)] in 15% acetic acid, a solution of sodium nitrite (1.55 g) in water (10 ml) was added dropwise. After stirring for one hour at 5°–10° C., the separated precipitate was filtered, crystallized from water, filtered again and dried under vacuum at 50° C. to give 3.44 g (77.5%) of the title compound, m.p. 226° C. (dec.).

Elemental Analysis: found: C, 30.11; H, 1.44; N, 42.00; Cl, 17.69; calculated for C$_5$H$_3$ClN$_6$O: C, 30.24; H, 1.52; N, 42.32; Cl, 17.85.

6-mercapto-8-aminocarbonyl-tetrazolo[1,5-b]pyridazine

To a stirred solution of NaSH.H$_2$O (10 g; 0.135 mole) in 150 ml of water, 6-chloro-8-aminocarbonyl-tetrazolo[1,5-b]pyridazine (10 g; 0.05 mole) was added and the mixture was vigorously stirred for 90 minutes. After cooling at 0° C., the reaction mixture was acidified with 23% HCl. After cooling at 0° C. for 1 hour, the solid was collected, washed with a little amount of cold water to give the title compound in quantitative yield, m.p. 185°–187° C. (dec.).

I.R. (Nujol):    —SH 2480 cm$^{-1}$
                 $\diagdown$C=O 1675 cm$^{-1}$
                 $\diagup$ T.L.C.: CHCl$_3$:CH$_3$OH:HCOOH=160:70:30 pure product U.V. (buffer phosphate at pH 7.4): $\lambda$max=262; E$_1$ cm$^{1\%}$=818

Elemental Analysis: found: C, 30.65; H, 2.00; N, 42.53; S, 16.16; calculated for C$_5$H$_4$N$_6$OS: C, 30.60; H, 2.05; N, 42.84; S, 16.34.

7-amino-3-[(8-aminocarbonyl-6-tetrazolo[1,5-b]pyridazinyl)-thiomethyl]-3-cephem-4-carboxylic acid To a hot solution (50°–55° C.) of 6-mercapto-8-aminocarbonyl-tetrazolo[1,5-b]pyridazine (2 g; 0.010 mole) and 2.8 g of sodium bicarbonate in 90 ml of buffer phosphate (pH 6.4), 7-ACA (4.6 g; 0.017 mole) was added portionwise and the mixture was heated at 60° C. for 4 hours. After cooling at 10° C. the precipitated 7-amino-3-[(8-aminocarbonyl-6-tetrazolo[1,5-b]pyridazinyl-thiomethyl]-3-cephem-4-carboxylic acid was collected by filtration. The solid was suspended in 150 ml of Me$_2$CO:H$_2$O (1:2), stirred for 30 minutes and filtered again. The collected precipitate was washed with Me$_2$CO and dried under vacuum at 60° C. to give the title compound (80%), m.p. 228°–230° C. (dec.).

Elemental Analysis: found: C, 37.93; H, 2.93; N, 27.13; S, 15.45; calculated for C$_{13}$H$_{12}$N$_8$O$_4$S$_2$: C, 38.22; H, 2.96; N, 27.43; S, 15.70.

I.R. (Nujol)    $\diagdown$C=O $\beta$-lactam 1780 cm$^{-1}$
                $\diagup$ U.V. (1% NaHCO$_3$) $\lambda$max=249; $\lambda$max=332.

EXAMPLE 3

By using the same method, the following compounds were obtained:

3-[(8-amino-6-tetrazolo[1,5-b]pyridazinyl)-thiomethyl]-7-[2-(2-amino-4-thiazolyl)-2-methoxyiminoacetamido]-1(R)-sulphinyl-3-cephem-4-carboxylic acid (syn-isomer);

3-[(8-amino-6-tetrazolo[1,5-b]pyridazinyl)-thiomethyl]-7-[2-(2-amino-4-thiazolyl)-2-methoxyiminoacetamido]-1(S)-sulphinyl-3-cephem-4-carboxylic acid (syn-isomer);

3-[(8-amino-6-tetrazolo[1,5-b]pyridazinyl)-thiomethyl]-7-[2-(2-amino-4-thiazolyl)-2-methoxyiminoacetamido]-1-sulphonyl-3-cephem-4-carboxylic acid (syn-isomer);

3-[(8-methylamino-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer).

EXAMPLE 4

3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer)

A stirred solution of anhydrous methylene chloride (200 ml) containing 2-(2-tritylamino-4-thiazolyl)-2-methoxyimino acetic acid (syn-isomer) (11.35 g; 0.0256 mole) and triethylamine (3.61 ml; 0.0256 mole), was cooled at 0° C. and phosphorus pentachloride (5.6 g; 0.027 mole) was added portionwise. After 15 minutes of stirring at 0° C. and 1 hour at room temperature, the mixture was evaporated under reduced pressure, taken up with anhydrous benzene, evaporated again in order to remove any trace of phosphorus oxychloride. This treatment was repeated twice (2×50 ml). The residue was suspended in 50 ml of anhydrous acetone; triethylamine hydrochloride was then removed by filtration. The acetone solution of 2-(2-tritylamino-4-thiazolyl)-2-methoxyiminoacetyl chloride thus obtained was dropped into a vigorously stirred ice-cooled solution of 7-amino-3-[(8-carboxy-6-tetrazolo[1,5-b]pyridazinyl)-thiomethyl]-3-cephem-4-carboxylic acid (10 g; 0.0232 mole) NaHCO$_3$ (15 g) in a mixture of water and acetone (500 ml; 250 ml). The mixture was stirred for 30 minutes at 0°-5° C. and then for 90 minutes at room temperature, the undissolved matter was filtered off, the acetone was eliminated by evaporation under vacuum. The aqueous phase was brought to pH 2 with 8% HCl and extracted with ethyl acetate (3×400 ml), washed with aqueous sodium chloride, dried (Na$_2$SO$_4$) and evaporated to dryness. The residue was stirred with diethyl ether; after 20 minutes of stirring the white solid was filtered, washed with ether and dried thus giving 3-[(8-carboxy-6-tetrazolo[1,5-b]pyridazinyl)-thiomethyl]-7-[2-(2-tritylamino-4-thiazolyl)-2-methoxyiminoacetamido]-3-cephem-4-carboxylic acid. The above mentioned compound was added portionwise to a stirred hot (55° C.) solution of 50% formic acid (140 ml). Stirring and heating at the same temperature was maintained for 30 minutes and then the solid was filtered from the cooled mixture. The filtrate was evaporated to dryness under vacuum, leaving a residue. After complete removal of water and formic acid, followed by trituration with water, a solid was obtained. The crude product was crystallized from 50% ethanol to give 9.1 g (60%) of the title compound, which decomposed at 255° C.

Elemental analysis: found: C, 38.10; H, 2.91; N, 23.34; S, 15.93; calculated for C$_{19}$H$_{16}$N$_{10}$S$_3$O$_7$: C, 38.50; H, 2.72; N, 23.63; S, 16.23.

T.L.C. (CHCl$_3$:MeOH:HCOOH:H$_2$O=140:75:20:20) R$_f$=0.25

I.R. (KBr)　　ν3500–2300 cm$^{-1}$ bonded —COOH

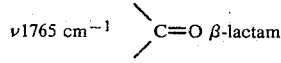 ν1765 cm$^{-1}$　C=O β-lactam

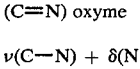

-continued

ν1710 cm$^{-1}$ C=O acid
1650 cm$^{-1}$ sec. amide
1620–1580 cm$^{-1}$ (C=N) oxyme, ν(C—N) + δ(N—H)
1540 cm$^{-1}$ ν(C—N) + δ(N—H) amide N.M.R., 100 MHz (DMSO-d$_6$) δp.p.m.
3.68 (1H, d, 2-CH$_2$)
3.86 (1H, d, 2-CH$_2$)
3.92 (3H, s, =N—OCH$_3$)
4.36 (1H, d, 3-CH$_2$—S)
4.69 (1H, d, 3-CH$_2$—S)
5.21 (1H, d, 6-H)
5.85 (1H, d-d, 7-H)
6.83 (1H, s, 5-H on thiazole ring)
7.30 (2H, br-s, —NH$_2$ on thiazole ring)
8.02 (1H, s, 7-H on pyridazine ring)
9.38 (1H, d, —CONH).

7-amino-3-[(8-carboxy-6-tetrazolo[1,5-b]pyridazinyl)-thiomethyl]-3-cephem-4-carboxylic acid used as starting material, was prepared as follows:

3-hydrazino-4-carboxy-6-chloro-pyridazine

A mixture of 3,6-dichloro-4-carboxy-pyridazine (20 g; 0.103 mole) and 22 ml of 98% hydrazine hydrate in 200 ml of 50% ethanol was refluxed, under stirring, for one hour. After cooling at 5° C., the solid precipitate was collected, washed with 20 ml of anhydrous ethanol. The solid was suspended in 100 ml of water, the mixture was brought to pH 1–2 with 23% HCl, after cooling at 5° C. the solid was filtered, dried under vacuum at 80° C. to give 18.29 g (93.4%) of the title compound, m.p. 198°–201° C.

Elemental analysis: found: C, 31.64; H, 2.64; N, 29.32; Cl, 18.53; calculated for C$_5$H$_5$ClN$_4$O$_2$: C, 31.84; H, 2.67; N, 29.71; Cl, 18.80.

N.M.R. (DMSO-d$_6$):　7.8 (1H,s,5-H on pyridazine ring)
9.2 (4H,br-s, —COOH, —NHNH$_2$)

6-chloro-8-carboxy-tetrazolo[1,5-b]pyridazine

To an ice-cold suspension of 3-hydrazino-4-carboxy-6-chloro-pyridazine (1.88 g; 0.01 mole) in 15% acetic acid, a solution of sodium nitrite (0.70 g) in water (5 ml) was added dropwise. After stirring for one hour at 5°–10° C. the separated precipitate was filtered, washed with anhydrous ethanol. The solid was suspended in 2 N HCl, the mixture was stirred for 30 minutes, the solid was stirred off, washed with cold water and dried under vacuum at 70° C. to give 1.73 g (87%) of the title compound, m.p. 225° C.

Elemental analysis: found: C, 29.95; H, 0.98; N, 35.15; Cl, 17.58; calculated for C$_5$H$_2$ClN$_5$O$_2$: C, 30.09; H, 1.00; N, 35.09; Cl, 17.76.

I.R. (Nujol):  C=O 1730 cm$^{-1}$

N.M.R. (DMSO-d$_6$): 8.33 (1H, s, 7-H on pyridazine ring)

6-mercapto-8-carboxy-tetrazolo[1,5-b]pyridazine

To a stirred solution of NaSH.H$_2$O (10 g; 0.135 mole) in 150 ml of water, 6-chloro-8-carboxy-tetrazolo[1,5-b]pyridazine (10 g; 0.05 mole) was added, and the mixture was vigorously stirred for 2 hours. After cooling at 0° C., the reaction mixture was acidified with 23% HCl. After cooling at 0° C. for 1 hour, the solid was collected, washed with a little amount of cold water, to give 9 g (91.5%) of the title compound, m.p. 210° C. (dec.).

Elemental analysis: found: C, 30.41; H, 1.52; N, 35.61; S, 16.19; calculated for C$_5$H$_3$N$_5$O$_2$S: C, 30.45; H, 1.53; N, 35.52; S, 16.26.

| I.R. (KBr) | (S—H) 2540 cm$^{-1}$ |
|---|---|
| | $\diagdown$C=O 1725 cm$^{-1}$ |

U.V. (buffer phosphate at pH 7.4) λmax=258 E$_1$ $_{cm}$$^{1\%}$=962

7-amino-3-[(8-carboxy-6-tetrazolo[1,5-b]pyridazinyl)-thiomethyl]-3-cephem-4-carboxylic acid To a hot solution (40° C.) of 6-mercapto-8-carboxy-tetrazolo[1,5-b]pyridazine (8.2g; 0.0415 mole) and 11.6 g of sodium bicarbonate in 265 ml of buffer phosphate (pH 6.4), 7-ACA (18.5 g; 0.068 mole) was added portionwise and the mixture was heated under stirring at 60° C. for 5 hours. After cooling at 20° C. the undissolved matter was filtered off, the solution was brought to pH 4.4 with 23% HCl. The precipitate was filtered, washed with a mixture of Me$_2$CO:H$_2$O (3:1) and then with Me$_2$CO to give the sodium salt of the title compound (75%), m.p.>270° C. (dec.)

Elemental analysis: found: C, 35.80; H, 2.66; N, 22.43; S, 14.66; Na, 5.10; calculated for C$_{13}$H$_{10}$N$_7$O$_5$S$_2$Na: C, 36.19; H, 2.33; N, 22.72; S, 14.86; Na, 5.32.

| I.R. (Nujol) | $\diagdown$C=O β-lactam 1770 cm$^{-1}$ |
|---|---|

U.V. (1% NaHCO$_3$): λmax=246; E$_1$ $_{cm}$$^{1\%}$=432

The sodium salt was suspended in water and acidified with 8% HCl so obtaining a solid, which was filtered, washed with water to give the title compound, m.p. 245° C. (dec.).

Elemental analysis: found: C, 38.45; H, 2.90; N, 23.55; S, 15.10; calculated for C$_{13}$H$_{11}$N$_7$O$_5$S$_2$: C, 38.13; H, 2.70; N, 23.94; S, 15.66.

EXAMPLE 5

3-[(8-amino-6-tetrazolo[1,5-b]pyridazinyl)thiomethyl]-7-[2-(2-amino-4-thiazolyl)-2-methoxyiminoacetamido]-3-cephem-4-carboxylic acid (syn-isomer)

N,N'-Dicyclohexylcarbodiimide (0.9 g; 0.00438 mole) was added to a cooled (0°-5° C.) solution of 2-(2-tritylamino-4-thiazolyl)-2-methoxyiminoacetic acid (3.675 g; 0.0828 mole) in anhydrous methylene chloride (13 ml). After stirring for 40 minutes at 5° C. and 30 minutes at room temperature the resulting slurry was diluted with anhydrous methylene chloride. The separated solid, viz. dicyclohexylurea (0.98 g, a quantitative yield), was filtered off and washed with fresh methylene chloride. The combined methylene chloride solutions were evaporated to dryness, thus giving the symmetrical anhydride of the starting acid, which was immediately taken up in anhydrous acetone (30 cc.). The above-obtained solution was dropped with stirring into an ice-bath cooled solution of 7-amino-3-[(8-amino-6-tetrazolo [1,5-b]pyridazinyl)-thiomethyl]-3-cephem-4-carboxylic acid (1.65 g; 0.00436 mole), triethylamine (1.22 ml; 0.00872 mole) and NaHCO$_3$ (0.347 g; (0.00414 mole) in 1:1 aqueous acetone (120 ml). After stirring for 1 hour at 0°-5° C. the ice-bath was removed and after another 2 hours the mixture was taken up in ethyl acetate (500 ml) and shaken with aqueous 1 N HCl (100 ml). The insoluble matter (a little amount of unreacted 7-amino-cephem) was filtered off, the organic layer was washed with aqueous sodium chloride solution, dried over Na$_2$SO$_4$, filtered and evaporated. A major part of the starting 2-(2-tritylamino-4-thiazolyl)-2-methoxyiminoacetic acid contained in the crude reaction mixture was precipitated from a dioxane solution (30 ml) by slowly adding dicyclohexylamine (1.4 ml). After 20 minutes at 12° C. this dicyclohexylamine salt was filtered off, the solution was diluted with ethyl acetate (200 ml), acidified with 1 N HCl, and the aqueous layer discarded. The organic phase was washed with aqueous sodium chloride solution, dried over Na$_2$SO$_4$, and concentrated to a small volume and added to diethyl ether, thereby giving 3.1 g of 3-[(8-amino-6-tetrazolo[1,5-b]pyridazinyl)-thiomethyl]-7-[2-(2-tritylamino-4-thiazolyl)-2-methoxyiminoacetamido]-3-cephem-4-carboxylic acid (syn-isomer). This material was treated with 50% aqueous formic acid as described in Example 1, thus giving the title compound which was shown by T.L.C., I.R. and N.M.R. to be identical to the product prepared in Example 1.

By using the same method, the following compounds were prepared:

3-[(8-amino-6-tetrazolo[1,5-b]pyridazinyl)-thiomethyl]-7-[2-(2-amino-4-thiazolyl)-2-cyanomethoxyiminoacetamido]-3-cephem-4-carboxylic acid (syn-isomer);

3-[(8-amino-6-tetrazolo[1,5-b]pyridazinyl)-thiomethyl]-7-[2-(2-amino-4-thiazolyl)-2-aminocarbonylmethoxyiminoacetamido]-3-cephem-4-carboxylic acid (syn-isomer);

3-[(8-amino-6-tetrazolo[1,5-b]pyridazinyl)-thiomethyl]-7-[2-(2-amino-4-thiazolyl)-2-carboxymethoxyiminoacetamido]-3-cephem-4-carboxylic acid (syn-isomer);

3-[(8-amino-6-tetrazolo[1,5-b]pyridazinyl)-thiomethyl]-7-[2-(2-amino-4-thiazolyl)-2-methoxyiminoacetamido]-1(R)-sulphinyl-3-cephem-4-carboxylic acid (syn-isomer);

3-[(8-amino-6-tetrazolo[1,5-b]-pyridazinyl)-thiomethyl]-7-[2-(2-amino-4-thiazolyl)-2-methoxyiminoacetamido]-1(S)-sulphinyl-3-cephem-4-carboxylic acid (syn-isomer);

3-[(8-amino-6-tetrazolo[1,5-b]pyridazinyl)-thiomethyl]-7-[2-(2-amino-4-thiazolyl)-2-methoxyiminoacetamido]-1-sulphonyl-3-cephem-4-carboxylic acid (syn-isomer);

3-[(8-aminocarbonyl-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer);

3-[(8-methylamino-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer).

EXAMPLE 6

3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer)

N,N'-Dicyclohexylcarbodiimide (0.9 g; 0.00438 mole) was added to a cooled (0°–5° C.) solution of 2-(2-tritylamino-4-thiazolyl)-2-methoxyiminoacetic acid (3.675 g; 0.0828 mole) in anhydrous methylene chloride (13 ml). After stirring for 40 minutes at 5° C. and 30 minutes at room temperature the resulting slurry was diluted with anhydrous methylene chloride. The separated solid, viz. dicyclohexylurea (0.98 g, a quantitative yield), was filtered off and washed with fresh methylene chloride. The combined methylene chloride solutions were evaporated to dryness, thus giving the symmetrical anhydride of the starting acid, which was immediately taken up in anhydrous acetone (30 cc.). The above-obtained solution was dropped with stirring into an ice-bath cooled solution of 7-amino-3-[(8-carboxy-6-tetrazolo[1,5-b]pyridazinyl)-thiomethyl]-3-cephem-4-carboxylic acid (1.78 g; 0.00436 mole), triethylamine (1.22 ml; 0.00872 mole) and NaHCO$_3$ (0.347 g; 0.00414 mole) in 1:1 aqueous acetone (120 ml). After stirring for 1 hour at 0°–5° C. the ice-bath was removed and after another 2 hours the mixture was taken up in ethyl acetate (500 ml) and shaken with aqueous 1 N HCl (100 ml). The insoluble matter (a little amount of ureacted 7-amino-cephem) was filtered off, the organic layer was washed with aqueous sodium chloride solution, dried over Na$_2$SO$_4$, filtered and evaporated. A major part of the starting 2-(2-tritylamino-4-thiazolyl)-2-methoxyiminoacetic acid contained in the crude reaction mixture was precipitated from a dioxane solution (30 ml) by slowly adding dicyclohexylamine (1.4 ml). After 20 minutes at 12° C. this dicyclohexylamine salt was filtered off, the solution was diluted with ethyl acetate (200 ml), acidified with 1 N HCl, and the aqueous layer discarded. The organic phase was washed with aqueous sodium chloride solution, dried over Na$_2$SO$_4$, and concentrated to a small volume and added to diethyl ether, thereby giving 3.3 g of 3-[(8-carboxy-6-tetrazolo[1,5-b]pyridazinyl)-thiomethyl]-7-[2-(2-tritylamino-4-thiazolyl)-2-methoxyiminoacetamido]-3-cephem-4-carboxylic acid (syn-isomer). This material was treated with 50% aqueous formic acid as described in Example 4, thus giving the title compound which was shown by T.L.C., I.R. and N.M.R. to be identical to the product prepared in Example 4.

EXAMPLE 7

3-[(8-amino-6-tetrazolo[1,5-b]pyridazinyl)thiomethyl]-7-[2-(2-amino-4-thiazolyl)-2-hydroxyiminoacetamido]-3-cephem 4-carboxylic acid (syn-isomer)

To a solution of 2-(2-tritylamino-4-thiazolyl)-2-trityloxyiminoacetic acid (2.25 g; 0.00335 mole) and triethylamine (0.47 ml; 0.00335 mole) in anhydrous methylene chloride cooled at −5° C., phosphorus pentachloride (0.697 g; 0.00335 mole) was added in one portion. After stirring for 20 minutes at −5° C. and 1 hour at room temperature, the reaction mixture was evaporated under reduced pressure without external heating until all POCl$_3$ had been pumped off. The residue was taken up in anhydrous acetone (50 ml) and the triethylamine hydrochloride was filtered off. The thus obtained acetone solution of 2-(2-tritylamino-4-thiazolyl)-2-trityloxyiminoacetyl chloride was dropped into a solution containing 7-amino-3-[(8-amino-6-tetrazolo[1,5-b]pyridazinyl)thiomethyl]-3-cephem-4-carboxylic acid (0.76 g; 0.002 mole), triethylamine (0.562 ml; 0.004 mole) and NaHCO$_3$ (0.281 g; 0.00335 mole) in water (35 ml) and acetone (25 ml) cooled at 0° C.

After the addition, the slurry was stirred at 0° C. for 30 minutes and then for 90 minutes at 25° C. The reaction mixture was poured into ethyl acetate (350 ml) with vigorous stirring; water (50 ml) was added and afterwards enough 2 N HCl was added to bring the aqueous phase to pH 2. The organic phase was separated, washed with aqueous sodium chloride solution, dried with Na$_2$SO$_4$ and evaporated to dryness. The resulting foam was triturated with diethyl ether to give 1.98 g of a crude product, containing a considerable amount of the starting acid. A major part of this contaminant was removed by dissolving the crude material in dioxane (10 ml) and dropping the resulting solution into diethyl ether (70 ml). After stirring for 10 minutes the white precipitate was collected by filtration, thus giving 3-[(8-amino-6-tetrazolo[1,5-b]pyridazinyl)-thiomethyl]-7-[2-(2-tritylamino-4-thiazolyl)-2-trityloxyiminoacetamido]-3-cephem-4-carboxylic acid (syn-isomer), (1.02 g).

The above-prepared compound (1 g) was added with stirring to a 50% aqueous formic acid solution (40 ml) kept at 55° C. (oil bath). After 35 minutes the mixture was cooled to 25° C. and filtered by suction; the solid was washed with fresh 50% formic acid (20 ml) and then with distilled water and discarded. The acidic solutions were combined and evaporated under reduced pressure. The residue was taken up in 99% ethanol and evaporated again, taken up in 99% ethanol, evaporated to a small volume (5 ml) and filtered. The resulting beige powder was dissolved in 2% aqueous NaHCO$_3$ solution (20 ml) and charcoal was added. The filtered solution was brought to pH 2 with 2 N HCl, and stirred for 5 minutes. The precipitate was collected by filtration, thoroughly washed with water and afterwards with small amounts of ethanol and dried at 65° C. for 16 hours, thus giving 0.25 g of 3-[(8-amino-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer) as an off-white powder, which decomposed at about 205° C. without melting.

Elemental analysis: Found: C, 36.81; H, 2.88; N, 27.73; S, 16.92; calculated for C$_{17}$H$_{15}$N$_{11}$O$_5$S$_3$: C, 37.15; H, 2.75; N, 28.03; S, 17.20.

I.R. (KBr) [cm$^{-1}$]:  3400  —NH
3000  —OH
1760  $\diagdown$C=O ($\beta$ lactam)  $\diagup$ NMR, 100 MHz (DMSO-d$_6$)
[δ,p.p.m.]:  3.61 (1H,d.,2-CH$_2$)    J ≃ 17 Hz
3.89 (1H,d.,2-CH$_2$)
4.16 (1H,d.,3-CH$_2$S)    J ≃ 13 Hz
4.60 (1H,d.,3-CH$_2$S)
5.21 (1H,d.,6-H)
5.86 (1H,d.d.,7-H
6.42 (1H,s.,7-H on pyridazine ring)
6.76 (1H,s.,5-H on thiazole ring)
7.20 (2H,broad s.,—NH$_2$ on thiazole ring)

| | |
|---|---|
| 8.02 (2H,broad s.,—NH₂ on pyridazine ring) | |
| 9.56 (1H,d.,—CONH—) | |
| 11.66 (1H,broad s.,=N—OH) | |

By using the same method compounds (6), (7), (10), (12), (14) and (16) of the Table were prepared.

EXAMPLE 8

3-[(8-amino-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer)

To a stirred solution of 3-acetoxymethyl-7-[2-(2-amino-4-thiazolyl)-2-methoxyiminoacetamido]-3-cephem-4-carboxylic acid (syn-isomer), (0.456 g, 0.001 mole) and NaHCO₃ (0.143 g, 0.0017 mole) in water (10 ml), 8-amino-6-mercapto-tetrazolo[1,5-b]pyridazine (0.118 g, 0.0007 mole) was added. A slow stream of nitrogen was passed through the solution, and the mixture was heated at 50° C. for 12 hours, while keeping the pH at 6.8. After cooling, the solution was acidified with 10% HCl, the precipitate collected by filtration, washed with water and then with ethanol. There was thus obtained 0.215 g of compound (2) which was shown by NMR, TLC and IR, to be identical to the product described in Example 1, apart a minor contaminant of the anti-isomer. By using the same method, the following compounds were prepared:

3-[(8-amino-6-tetrazolo[1,5-b]pyridazinyl)-thiomethyl]-7-[2-(2-amino-4-thiazolyl)-2-methoxyiminoacetamido]-1(R)-sulphinyl-3-cephem-4-carboxylic acid (syn-isomer);

3-[(8-amino-6-tetrazolo[1,5-b]pyridazinyl)-thiomethyl]-7-[2-(2-amino-4-thiazolyl)-2-methoxyiminoacetamido]-1(S)-sulphinyl-3-cephem-4-carboxylic acid (syn-isomer);

3-[(8-amino-6-tetrazolo[1,5-b]pyridazinyl)-thiomethyl]-7-[2-(2-amino-4-thiazolyl)-2-methoxyiminoacetamido]-1-sulphonyl-3-cephem-4-carboxylic acid (syn-isomer);

3-[(8-aminocarbonyl-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer);

3-[(8-methylamino-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer);

3-[(8-carboxy-6-tetrazolo[1,5-b]pyridazinyl)-thiomethyl]-7-[2-(2-amino-4-thiazolyl)-2-ethoxyiminoacetamido]-3-cephem-4-carboxylic acid (syn-isomer);

3-[(8-carboxymethyl-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer);

3-[(8-β-carboxyethyl-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer).

EXAMPLE 9

3-[(8-amino-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer)

To a stirred solution of 3-acetoxymethyl-7-[2-(2-tritylamino-4-thiazolyl)-2-methoxyiminoacetamido]-3-cephem-4-carboxylic acid (0.697 g; 0.001 mole) in anhydrous acetonitrile (50 ml), 8-amino-6-mercaptotetrazolo[1,5-b]pyridazine (0.336 g; 0.002 mole) was added and the resulting slurry was refluxed under a slow stream of nitrogen for 24 hours. Another portion of the mercapto compound (0.168 g; 0.001 mole) was added, and after further 16 hours of stirring at the reflux temperature, the mixture was cooled, the undissolved matter (unreacted mercapto compound) filtered off, the acetonitrile solution evaporated to dryness, the resulting foam taken up in warm methylene chloride (5 ml) and diethyl ether added (25 ml). The resulting white precipitate was collected by filtration and washed with a small amount of ethyl acetate and then with diethyl ether, thus giving 0.650 g of 3-[(8-amino-6-tetrazolo[1,5-b]pyridazinyl)-thiomethyl]-7-[2-(2-tritylamino-4-thiazolyl)-2-methoxyiminoacetamido]-3-cephem-4-carboxylic acid (syn-isomer). This material was reacted with 50% aqueous formic acid, as described in Example 1, thus giving the title product, which was shown by T.L.C., I.R. and NMR to be identical to the product prepared in Example 1.

By using the same method the following compounds were prepared:

3-[(8-amino-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer);

3-[(8-carboxy-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer);

3-[(8-aminocarbonyl-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer);

3-[(8-aminocarbonyl-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer);

3-[(8-methylamino-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer);

3-[(8-methylamino-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer);

3-[(8-carboxy-6-tetrazolo[1,5-b]pyridazinyl)-thiomethyl]-7-[2-(2-amino-4-thiazolyl)-2-ethoxyiminoacetamido]-3-cephem-4-carboxylic acid (sym-isomer);

3-[(8-carboxymethyl-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer);

3-[(8-β-carboxyethyl-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer).

EXAMPLE 10

3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer)

To a stirred solution of 3-acetoxymethyl-7-[2-(2-amino-4-thiazolyl)-2-methoxyiminoacetamido]-3-cephem-4-carboxylic acid (syn-isomer) (0.456 g, 0.001 mole) and NaHCO$_3$ (0.143 g, 0.0017 mole) in water (10 ml), 8-carboxy-6-mercapto-tetrazolo[1,5-b]pyridazine (0.138 g, 0.0007 mole) was added. A slow stream of nitrogen was passed through the solution, and the mixture was heated at 50° C. for 12 hours, while keeping the pH at 6.8. After cooling, the solution was acidified with 10% HCl, the precipitate collected by filtration, washed with water and then with ethanol. There was thus obtained 0.245 g of the title compound which was shown by N.M.R., T.L.C. and I.R. to be identical to the product described in Example 4, apart a minor contaminant of the anti-isomer.

EXAMPLE 11

3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer)

To a stirred solution of 3-acetoxymethyl-7-[2-(2-tritylamino-4-thiazolyl)-2-methoxyiminoacetamido]-3-cephem-4-carboxylic acid (0.697 g, 0.001 mole) in anhydrous acetonitrile (50 ml), 8-carboxy-6-mercapto-tetrazolo[1,5-b]pyridazine (0.394 g, 0.002 mole) was added and the resulting slurry was refluxed under a slow stream of nitrogen for 24 hours.

Another portion of the mercapto compound (0.168 g, 0.001 mole) was added, and after further 16 hours of stirring at the reflux temperature, the mixture was cooled, the undissolved matter (unreacted mercapto compound) filtered off, the acetonitrile solution evaporated to dryness, the resulting foam taken up in warm methylene chloride (5 ml) and diethyl ether added (25 ml). The resulting white precipitate was collected by filtration and washed with a small amount of ethyl acetate and then with diethyl ether, thus giving 0.730 g of 3-[(8-carboxy-6-tetrazolo[1,5-b]pyridazinyl)thiomethyl]-7-[2-(2-tritylamino-4-thiazolyl)-2-methoxyiminoacetamido]-3-cephem-4-carboxylic acid (syn-isomer). This material was reacted with 50% aqueous formic acid, as described in Example 4 thus giving the title product, which was shown by T.L.C., I.R. and NMR to be identical to the product prepared in Example 4.

EXAMPLE 12

3-[(8-amino-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer)

Step A: 4-chloroacetoacetic acid

Ethyl 4-chloroacetoacetate (30 g; 0.182 mole) was stirred with 37% aqueous HCl (200 ml) at room temperature for 15 hours, after which time the reaction mixture was poured into ice/water, extracted with ethyl acetate, dried over Na$_2$SO$_4$ and evaporated to dryness without external heating, thus giving 17.4 g (70% yield) of 4-chloroacetoacetic acid. The crude material was used in the next step without further purification.

| N.M.R. 60 MHz (CDCl$_3$): | 3.71 (2H,s.,COCH$_2$COOH) |
|---|---|
| | 4.20 (2H,s.,ClCH$_2$CO) |
| | 9.98 (1H,broad s.,COOH) |

Step B: 4-chloroacetoacetyl chloride

Oxalyl chloride (1.71 ml; 0.02 mole) was added to a solution of 4-chloroacetoacetic acid (2.4 g; 0.017 mole) in anhydrous benzene, followed by a drop of N,N-dimethylformamide. After stirring for 15 hours at 25° C., the solution was evaporated to dryness, taken up in anhydrous benzene, and evaporated again, thus giving 2.7 g of a dark oily product which was used as such in the following acylation step (Step C). Alternatively, 4-chloroacetoacetyl chloride can be prepared by reacting diketene, dissolved in a suitable inert solvent, e.g. methylene chloride, with chlorine, according to the method described in *Helv. Chim. Acta,* 60, 1256 (1977).

Step C: 3-[(8-amino-6-tetrazolo[1,5-b]pyridazinyl)-thiomethyl]-7-(4-chloro-3-oxobutyramido)-3-cephem-4-carboxylic acid 7-Amino-3-[(8-amino-6-tetrazolo[1,5-b]pyridazinyl)-thiomethyl]-3-cephem-4-carboxylic acid (3.8 g; 0.01 mole) was suspended in anhydrous N,N-dimethylformamide (50 ml) and N,O-bis(trimethylsilyl)acetamide (8.13 g; 0.04 mole) was added. After 2 hours of stirring at room temperature almost all the starting material was dissolved. A solution of 4-chloroacetoacetyl chloride (2.35 g; approximately 0.015 mole) in anhydrous methylene chloride (20 cc) was dropped into the cooled mixture (at −30° C.). The mixture was stirred at −30° C. for 2 hours and allowed to come to room temperature within an additional hour, after which time isopropanol (40 ml) was added, in order to decompose the silylated compounds. The solvents were evaporated under reduced pressure and the oily residue was partitioned between water and ethyl acetate. The organic layer was separated, washed with aqueous sodium chloride solution, concentrated to a small volume under reduced pressure, and diethyl ether was added to complete the precipitation. The solid was collected by filtration, washed with fresh ether and dried under vacuum, thus giving 4.6 g of the title compound, which was used in the following step without further purification.

N.M.R., 60 MHz (DMSO-d$_6$)

| [δ,p.p.m.]: | 3.6–3.7 (4H,s + d.d.,2-CH$_2$ + COCH$_2$CO) |
|---|---|
| | 4.35 (2H,d.d.,3-CH$_2$S) |
| | 4.57 (2H,s.,Cl-CH$_2$CO) |
| | 5.08 (1H,d.,6-H) |
| | 5.69 (1H,d.d.,7-H) |
| | 6.38 (1H,s.,7-H on pyridazine ring) |
| | 7.95 (2H,broad s., —NH$_2$ on pyridazine ring) |
| | 9.02 (1H,s., CONH) |

Step D: 3-[(8-amino-6-tetrazolo[1,5-b]pyridazinyl)thiomethyl]-7-(4-chloro-2-hydroxyimino-3-oxobutyramido)-3-cephem-4-carboxylic acid (syn-isomer)

To a stirred solution of 3-[(8-amino-6-tetrazolo[1,5-b]pyridazinyl)thiomethyl]-7-(4-chloro-3-oxobutyramido)-3-cephem-4-carboxylic acid (6.72 g; 0.0171 mole) in acetic acid (60 ml), a solution of sodium nitrite (1.65 g; 0.0239 mole) in water (6 ml) was added at 5°–10° C. After stirring for 3.5 hours at room temperature, the reaction mixture was quenched with brine and extracted with ethyl acetate (4×200 ml). The combined extracts were washed with water, dried over Na$_{SO4}$ and evaporated to a foam. Trituration of this product with diethyl ether afforded the title compound as a beige powder, 6.3 g.

TLC (silica gel plates, CHCl$_3$/MeOH/HCOOH 160:40:20) revealed a single spot, with a slightly smaller R$_f$ value then the starting material.

NMR, 60 MH$_z$ (DMSO-d$_6$)

| [δ,p.p.m.]: | 3.60 (2H,d.d.,2-CH$_2$) |
|---|---|
| | 4.35 (2H,d.d.,3-CH$_2$S) |
| | 4.74 (2H,s.,ClCH$_2$CO) |
| | 5.08 (1H,d.,6-H) |
| | 5.70 (1H,d.d.,7-H) |
| | 6.38 (1H,s.,7-H on pyridazine ring) |
| | 7.96 (2H broad s, —NH$_2$ on pyridazine ring) |
| | 9.21 (1H,d.,—CONH—) |
| | 13.00 (1H,s., =N—OH) |

Step E:
3-[(8-amino-6-tetrazolo[1,5-b]pyridazinyl)thiomethyl]-7-[2-(2-amino-4-thiazolyl)-2-hydroxyiminoacetamido]-3-cephem-4-carboxylic acid (syn-isomer), compound (1)

3-[(8-amino-6-tetrazolo[1,5-b]pyridazinyl)thiomethyl]-7-(4-chloro-2-hydroxyimino-3-oxobutyramido)-3-cephem-4-carboxylic acid (5.12 g; 0.01 mole) was dissolved in anhydrous N,N-dimethylacetamide (25 ml). Thiourea (0.76 g; 0.01 mole) was added, and the mixture was stirred at room temperature for 3 hours. The resulting solution was dropped under stirring into ethyl acetate (250 ml). A gummy material precipitated; the supernatant mother liquors were discarded and the residue was carefully triturated with fresh ethyl acetate until a powder was obtained. The powder was collected by filtration and dried. There was thus obtained a N,N-dimethylacetamide solvate of the hydrochloride salt of the desired product. This material was dissolved in aqueous NaHCO$_3$ and washed five times with ethyl acetate, then with diethyl ether. Nitrogen was bubbled in for 15 minutes, charcoal was added, the charcoal was filtered off and the solution made acidic with 2 N HCl. The crystalline precipitate was collected and thoroughly washed with water and then with ethyl alcohol, yielding 3.8 g of the title compound, identical by TLC, IR, NMR to the product prepared in Example 7.

By using the same method, the following compounds were prepared:

3-[(8-amino-6-tetrazolo[1,5-b]pyridazinyl)-thiomethyl]-7-[2-(2-amino-4-thiazolyl)-2-hydroxyiminoacetamido]-1(R)-sulphinyl-3-cephem-4-carboxylic acid (syn-isomer);

3-[(8-amino-6-tetrazolo[1,5-b]pyridazinyl)-thiomethyl]-7-[2-(2-amino-4-thiazolyl)-2-hydroxyiminoacetamido]-1(S)-sulphinyl-3-cephem-4-carboxylic acid (syn-isomer);

3-[(8-amino-6-tetrazolo[1,5-b]pyridazinyl)-thiomethyl]-7-[2-(2-amino-4-thiazolyl)-2-hydroxyiminoacetamido]-1-sulphonyl-3-cephem-4-carboxylic acid (syn-isomer);

3-[(8-carboxy-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer);

3-[(8-aminocarbonyl-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer);

3-[(8-methylamino-6-tetrazolo[1,5-b]pyridazinyl)-thiomethyl]-7-[2-(2-amino-4-thiazolyl)-2-hydroxyiminoacetamido]-3-cephem-4-carboxylic acid (syn-isomer).

EXAMPLE 13

To an aqueous suspension of 3-[(8-amino-6-tetrazolo[1,5-b]pyridazinyl-thiomethyl]-7-[2-(2-amino-4-thiazolyl)-2-methoxyiminoacetamido]-3-cephem-4-carboxylic acid (syn-isomer) (5.63 g) in water (80 ml), the stoichiometric amount of NaHCO$_3$ was added, so obtaining the complete solution of the compound. This solution was then lyophilized so obtaining the sodium salt of 3-[(8-amino-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer), m.p. >240° C. (dec.).

Elemental analysis: found: Na, 3.80; calculated: Na, 3.90.

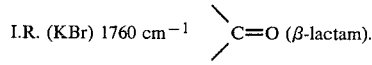

I.R. (KBr) 1760 cm$^{-1}$ ⟩C=O (β-lactam).

EXAMPLE 14

To an aqueous suspension of 3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer), (5.92 g) in water (80 ml), two equivalents of NaHCO$_3$ were added, so obtaining the complete solution of the compound. This solution was then lyophilized so obtaining the disodium salt of 3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer), m.p. >270° C. (dec.).

Elemental analysis: found: Na, 6.91; calculated: Na, 7.19.

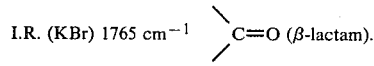

I.R. (KBr) 1765 cm$^{-1}$ ⟩C=O (β-lactam).

EXAMPLE 15

To a solution of 3-[(8-carboxy-6-tetrazolo[1,5-b]pyridazinyl)-thiomethyl]-7-[2-(2-amino-4-thiazolyl)-2-methoxyimino-acetamido]-3-cephem-4-carboxylic acid (syn-isomer), (5.92 g) in acetone (400 ml), two equivalents of a 30% solution of sodium 2-ethylhexanoate in isopropyl alcohol were added. After stirring for 30 minutes at room temperature, the mixture was diluted with petroleum ether and the obtained precipitate was filtered to give the disodium salt of 3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer), m.p. >270° C. (dec.).

Elemental analysis: found: Na, 6.91; calculated: Na, 7.19.

I.R. (KBr) 1765 cm$^{-1}$ $\diagdown$C=O ($\beta$-lactam).

EXAMPLE 16

An injectable pharmaceutical composition was performed by dissolving 100–500 mg of disodium salt of 3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer) in sterile water or sterile normal saline solution (1–2 ml).

We claim:

1. 3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid and its pharmaceutically and veterinarily acceptable salts.

2. 3-[(8-carboxy-6-tetrazolo[1,5-b]pyridazinyl)-thiomethyl]-7-[2-(2-amino-4-thiazolyl)-2-methoxyiminoacetamido]-3-cephem-4-carboxylic acid (syn-isomer) and its pharmaceutically and veterinarily acceptable salts.

3. Method of treating gram-positive or gram-negative bacteria infection in a patient, said method comprising administering to said patient a therapeutically effective amount of a compound of claim 1 or 2.

4. Method of claim 3, wherein said bacteria infection is a Gram-negative bacteria infection.

5. An anti-bacterial pharmaceutical or veterinary composition comprising a compound of claim 1 or 2 and a pharmaceutically or veterinarily acceptable carrier therefor.

* * * * *